(12) United States Patent
Gavish

(10) Patent No.: US 9,655,549 B2
(45) Date of Patent: May 23, 2017

(54) FLEXIBLE CAPACITIVE PRESSURE SENSOR AND RESPIRATION MONITOR USING THE SAME

(71) Applicant: Benjamin Gavish, Eshtaol (IL)

(72) Inventor: Benjamin Gavish, Eshtaol (IL)

(73) Assignee: 2BREATHE TECHNOLOGIES LTD., Eshtaol (IL)

( * ) Notice: Subject to any disclaimer, the term of this patent is extended or adjusted under 35 U.S.C. 154(b) by 0 days.

(21) Appl. No.: 14/848,379

(22) Filed: Sep. 9, 2015

(65) Prior Publication Data

US 2017/0035329 A1    Feb. 9, 2017

(30) Foreign Application Priority Data

Aug. 9, 2015 (IL) .......................................... 240460

(51) Int. Cl.
| | |
|---|---|
| *G01B 5/30* | (2006.01) |
| *A61B 5/11* | (2006.01) |
| *A61B 5/08* | (2006.01) |
| *G01L 1/14* | (2006.01) |
| *A61B 5/113* | (2006.01) |

(52) U.S. Cl.
CPC .......... *A61B 5/1126* (2013.01); *A61B 5/0816* (2013.01); *A61B 5/1135* (2013.01); *G01L 1/146* (2013.01); *A61B 2562/0233* (2013.01); *A61B 2562/0247* (2013.01)

(58) Field of Classification Search
CPC .......... G01L 1/205; G01L 1/142; G01N 3/02; A61B 5/1135; A61B 5/1126; A61B 2562/0247; G01B 7/16

USPC ............. 73/760, 780, 862.046, 862.639, 789
See application file for complete search history.

(56) References Cited

U.S. PATENT DOCUMENTS

| | | | | |
|---|---|---|---|---|
| 4,852,443 A | * | 8/1989 | Duncan | ................ G10H 1/0551 200/600 |
| 4,933,807 A | * | 6/1990 | Duncan | ................ G10H 1/0551 361/283.2 |
| 4,986,136 A | | 1/1991 | Brunner | |

(Continued)

FOREIGN PATENT DOCUMENTS

EP         2899521 A1     7/2015

OTHER PUBLICATIONS

International Search Report and Written Opinion for PCT/IL2016/050853, mailed Nov. 16, 2016.

*Primary Examiner* — Max Noori
(74) *Attorney, Agent, or Firm* — Peter A. Nieves; Sheehan Phinney Bass & Green PA

(57) ABSTRACT

A capacitive pressure sensor includes first and second of mutually displaceable elastic members each having a respective electrically conductive surface separated by a thin elastic dielectric. Variations in area of pressure-induced contact between the first and second members are used to vary capacitance of the sensor that allows determination of differential pressure between the two elastic members. Both of the elastic members have respective projections, the projections of the first elastic member being disposed in interlocking relationship with the projections of the second elastic member and configured so that as the elastic members are pressed toward each other their respective projections progressively engage and create increasing areas of contact.

12 Claims, 16 Drawing Sheets

(56) References Cited

U.S. PATENT DOCUMENTS

| | | | | |
|---|---|---|---|---|
| 6,234,031 B1* | 5/2001 | Suga | ............... | G06K 9/0002 |
| | | | | 73/862.474 |
| 7,909,637 B2* | 3/2011 | Montena | ............ | H01R 13/6683 |
| | | | | 439/489 |
| 2001/0020578 A1* | 9/2001 | Baier | ............... | H03K 17/96 |
| | | | | 200/600 |
| 2010/0315373 A1* | 12/2010 | Steinhauser | ............ | G01L 1/205 |
| | | | | 345/174 |
| 2014/0253305 A1* | 9/2014 | Rosenberg | ............. | G06F 3/016 |
| | | | | 340/407.2 |

\* cited by examiner

FIG. 3
(Prior Art)
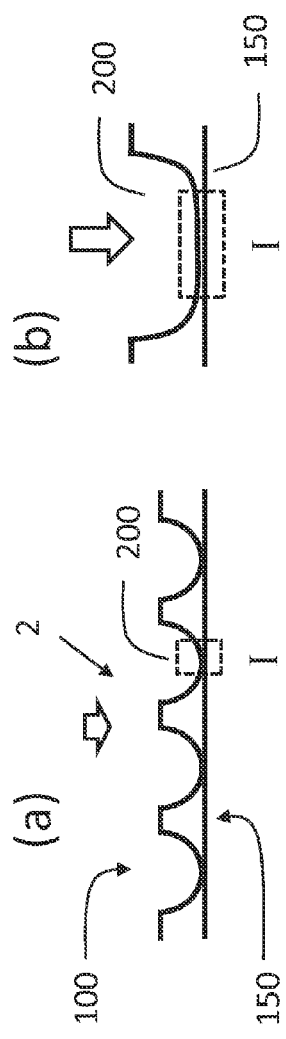
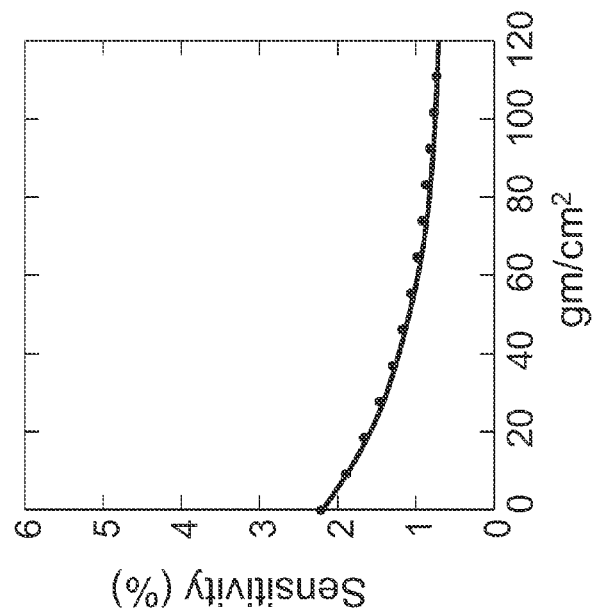
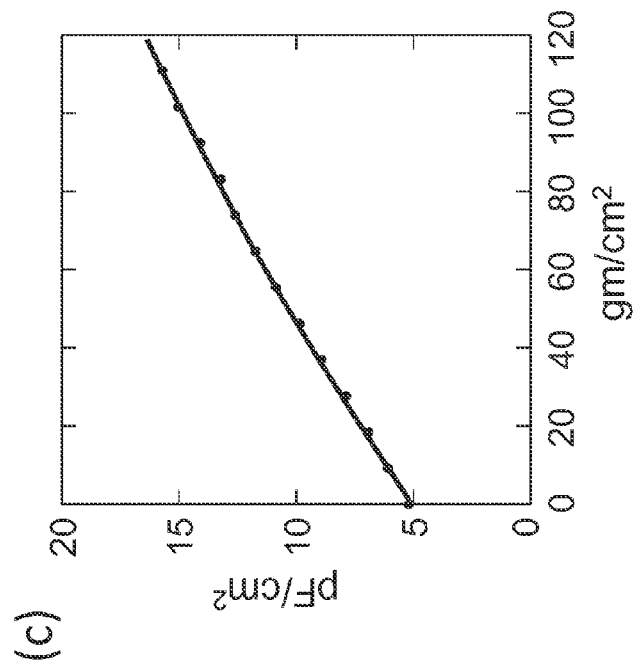

FIG. 7
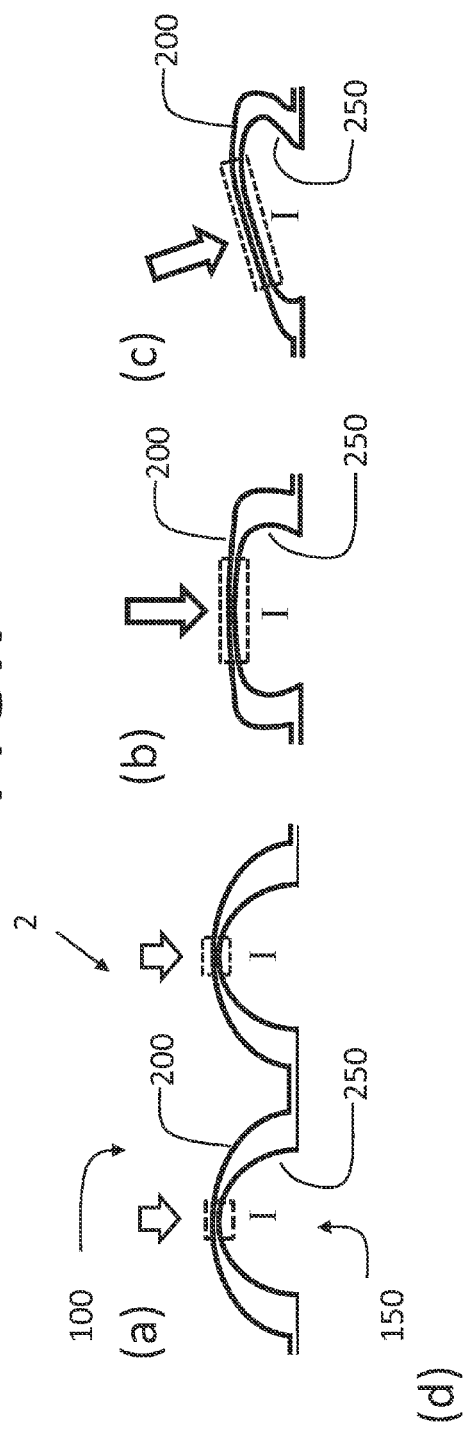
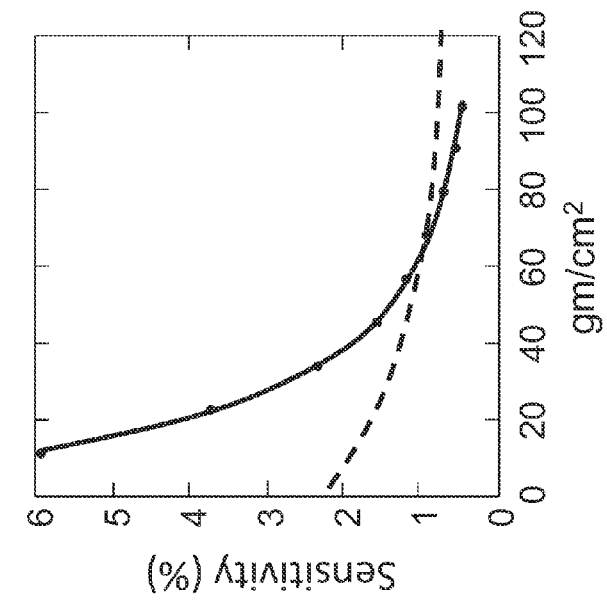
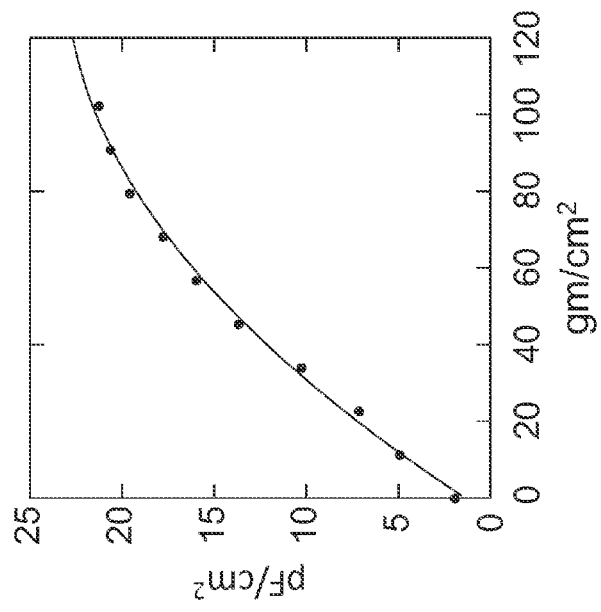

FLEXIBLE CAPACITIVE PRESSURE SENSOR AND RESPIRATION MONITOR USING THE SAME

CROSS-REFERENCE TO RELATED APPLICATIONS

This application claims priority to Israel Patent Application serial number IL240460, filed Aug. 9, 2015, which is incorporated by reference herein in its entirety.

FIELD OF THE INVENTION

The present invention generally relates to systems and methods to convert pressure into capacitance using a flexible sensor and particularly for monitoring body movements and respiration using such a sensor.

BACKGROUND OF THE INVENTION

The fast development of healthcare technology increases the need for monitoring respiration via the pressure exerted by the human body on appliances, such as a mattress (during sleep), chair and sofa without wearing a sensor. Some applications require a respiration signal to be both DC and relatively noiseless at high-enough quality that enables detection in real time of the onset of breathing phases, e.g. expiration, and breath holding. Such applications may include, for example, breathing pattern modification using guiding tones, as applied by a device called RESPeRATE for inducing relaxation and treating hypertension. This device is described in U.S. Pat. No. 5,800,337. For such applications the sensor should be thin enough not to cause the user any discomfort; flexible, as both the relevant appliances and the human body are usually deformable and soft; highly sensitive, as the pressure modulation elicited by respiration is rather small, and inexpensive, as the main market is for home use. For these reasons, piezo-based sensors that provide AC signals are not optimal.

Flexible sensors that convert pressure into capacitance seem to be appropriate for this purpose. In general, two conductive surfaces of area A separated by a dielectric of thickness d generate capacitance C that is proportional to A/d. Noda et at. (U.S. Pat. No. 7,641,618) disclose a capacitance-based pad sensor for heart/respiration monitoring in bed, in which the dielectric is flexible, resulting in the increase of capacitance, C from its unloaded value due to the reduction of d under loading. Brunner et al. (U.S. Pat. No. 4,986,136) disclose a sensitive capacitance-based pressure measurement system, with an upper conductive surface that includes deformable projections that contact, via a thin dielectric, a lower flat conductive surface (FIG. 3a). The capacitance of this structure increases in response to applied pressure, as the contact area between the upper and the lower conductive surfaces increases due to the deformation of the projections (FIG. 3b). Alternatively, as shown in FIG. 8 thereof both upper- and lower conductive surfaces contain mutually opposed parallel strip-like tapered projections that are oriented to each other preferably at right angles. Respective strips of projections in the upper and lower surface intersect thereby forming a plurality of capacitive cells. The capacitance of the sensor may therefore be considered as a matrix of parallel rows of series connected capacitive cells. In an initial displacement of the upper and lower surfaces, the tips of the projections are undistorted and define very low areas of mutual contact pressure. As the surfaces are urged toward each other, the tips of the projections become progressively flattened thus creating progressively increasing areas of pressure contact. Additionally, the distance between the two surface decreases, which further increases the capacitance. It is to be noted, however, that because the projections of the two surfaces are mutually offset, as indeed they must be to create a matrix of capacitive cells, only their respective tips contribute to the increasing areas of pressure contact. Therefore, at no stage during use of the sensor is there any ability for the opposing projections of the two surfaces to interlock or otherwise engage.

U.S. Pat. No. 4,437,138 discloses a force sensor comprising capacitor plates formed of metallic cloth bonded to a compressible elastomeric dielectric. The metallic cloth strips are in the form of strips running crosswise on opposite sides of the dielectric to provide a matrix of force sensors. The warp and weft threads of the metallic cloth increase the flexibility of the sensor but the warp and weft threads of one plate do not interlock with or otherwise engage the warp and weft threads of the other plate or affect the capacitance of the sensor, which is determined only by the compression of the intermediate dielectric.

SUMMARY OF THE INVENTION

One object of the present invention is to provide a more sensitive flexible capacitive pressure sensor.

It is another object of the invention to use such a sensor in an apparatus for monitoring respiration and other body-generated movements at high sensitivity, very low signal-to-noise ratio, and without restraining the user.

These objects are achieved in accordance with a broad aspect of the invention by a capacitive pressure sensor comprising first and second mutually displaceable elastic members each having a respective electrically conductive surface separated by a thin elastic dielectric, wherein:

variations in area of pressure-induced contact between the first and second members are used to vary capacitance of the sensor that allows determination of differential pressure between the two elastic members; and both of the elastic members have respective projections, the projections of the first elastic member being disposed in interlocking relationship with the projections of the second elastic member and configured so that as the elastic members are pressed toward each other their respective projections progressively engage and create increasing areas of contact.

In some embodiments, the projections are realized by a concave cavity and in others by a convex protrusion. It will be appreciated that both concave and convex structures may be regarded as projections since they are formed not in the surface of the elastic members but rather by these surfaces. Consequently, whether a projection appears convex or concave is solely dependent on the direction in which the elastic members are viewed: from one side the projections will appear as convex protrusions and from the opposite side they will appear as concave cavities.

The term "interlocking" as used in the description and the appended claims means that the respective projections in the opposing surfaces engage each other in such a manner that they cannot be completely separated by lateral displacement along two mutually orthogonal axes. To qualify and clarify this, there is no requirement that the interlocking be tight and consequently, there is no requirement that lateral displacement to any extent must be impeded. The projections may interlock loosely such that some degree of lateral displacement is possible, but not to the extent that the two surfaces can be completely separated along both axes.

In accordance with another aspect of the invention, there is provided a capacitive pressure sensor comprising first and second mutually displaced elastic members each having a respective electrically conductive surface separated by a thin elastic dielectric, each of the elastic members having at least one respective contact area, the respective contact areas being configured to effect pressure-induced contact as compression is applied to the displaced elastic members, wherein:

variations in the areas of contact pressure between the two members are used to vary capacitance that allows measurement of the compression;

the respective contact areas of the first and second elastic members each have at least one finite radius of curvature; and at each point of pressure-induced contact between the two elastic members, all of the respective radii of curvature of both elastic members are oriented in an identical direction.

A major benefit of the present invention over known structures is in the enhanced sensitivity of a capacitive-based pressure sensor due principally to the fact that interlocking projections offer increased rate of change in areas of contact per unit of pressure as the surfaces are pressed together. Specifically, areas on the side surfaces of the projections effect mutual contact and the projections may be shaped to ensure that significantly larger areas of the projections mutually engage even in response to a relatively small increase in pressure. This greatly enhances the sensitivity of the sensor.

In some embodiments, the elastic members and include projections with one-dimensional symmetry, e.g. parallel projections or tubes located on the X-Y plane, or two-dimensional symmetry, e.g. the projections have the form of half ellipsoids arranged as an array on the X-Y plane, or three-dimensional symmetry, e.g. plain weave structure, or any combination of the above-mentioned embodiments.

In some embodiments, there is provide a sleep monitor using a flexible sensor that has at least one sensing unit that is subject to pressure exerted by the user body on a support that are both, in general, deformable and not planar, in an attempt to monitor desired variables that include at least respiratory movements. Some embodiments include a pad-like flexible sensor used on a mattress, or on the back of a chair or sofa; a flexible sensor integrated into a neck supporting pillow sensor, and a belt-type respiration sensor.

In embodiments where the flexible sensor includes more than one sensing unit the capacitance of the individual sensing units may be connected to a capacitance-to-data converter via a multiplexer that is operative to connect the sensing units in a selected order and timing controlled by the system.

In some embodiments, multiple sensing units are provided to measure variation in pressure distribution over time, possibly as a measure for body movements.

In some embodiments, raw or analyzed sensor data are transmitted to a host device, which performs at least one of the following functions:

generating stimulus input to user that may be used in affecting respiration and other body movements in a closed or open loop;

generating stimulus input to appliances; providing indication inputs to user; data storage and communicating with a remote site;

receiving user commands; and controlling the operation of an electronic sensor circuit via bi-directional communication.

In embodiments where the raw data are transmitted to the host device, the latter also performs the data analysis to obtain the desired variables.

In some embodiments, the host device is a hand-held device such as a mobile phone, iPad, iPod, laptop, etc. which may effect bi-directional communication with the electronic circuit using Bluetooth™ low energy (BLE) technology or another suitable short-range protocol.

In some embodiments, the host device generates in real time audiovisual or tactile stimuli in response to monitored body movements. The user synchronizes with these stimuli body movements, preferably respiration, in a way that leads gradually to modification of these movements in a desired direction known to be beneficial to the user. For example, slowing respiration and relatively prolonging exhalation induces relaxation and sleep. It will be appreciated that the generating stimuli in response to single- or multiple respiration patterns, or to non-respiratory movements, may be useful for detracting the user attention from wondering thoughts and external stimuli that interfere with falling asleep or relax.

In some embodiments, an electronic circuit switches its mode of operation between inactive and active states, depending on whether the flexible sensor is unloaded or loaded, respectively.

In some embodiments, real-time or nearly real-time analysis of sensed data from multiple sensors is applied in attempt to select the sensor that provides the best quality desired variable. The selection process may be repeated, if necessary and the user may be notified if selection fails. In some embodiments, the desired variable is indicative of respiration.

In some embodiments, there is provided a sleep monitor comprising a pad-like flexible sensor with multiple sensing units. The sensor contains an electronic circuit that communicates bi-directionally with a host device, preferably a mobile phone for monitoring body pressure distribution on the pad, respiratory movements using automatically selected sensing units and body movements unrelated to respiration.

BRIEF DESCRIPTION OF THE DRAWINGS

In order to understand the invention and to see how it may be carried out in practice, embodiments will now be described, by way of non-limiting example only, with reference to the accompanying drawings, in which:

FIG. 3 includes a cross-sectional view of a prior art sensing unit and graphs that depict its performance under variable pressure;

FIG. 7 includes a sectional view of the sensing unit employed in the system of FIG. 1 and graphs that depict its performance under variable pressure, in accordance with another embodiment of the present invention;

DETAILED DESCRIPTION OF EMBODIMENTS

In the following description of some embodiments, identical components that appear in more than one figure or that share similar functionality will be referenced by identical reference symbols.

Figure 1:
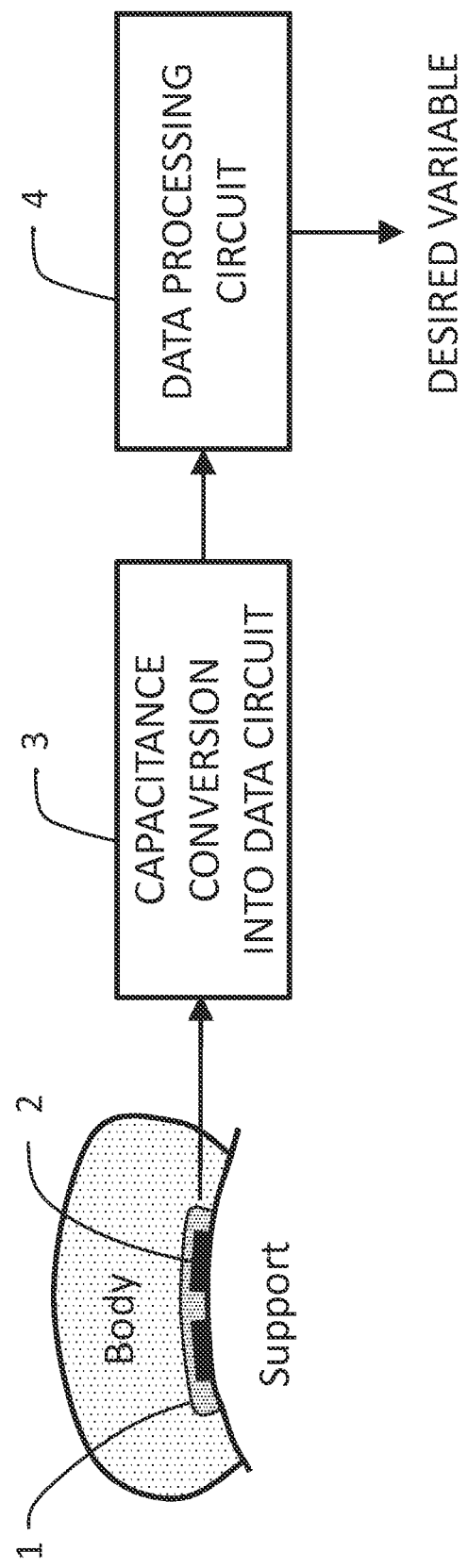
FIG. 1 is a block diagram of a prior art monitor suitable for use with an embodiment of the present invention.

FIG. 1 illustrates a sleep monitor comprising a flexible capacitive pressure sensor 1 placed between and compressed by the human body and a support that are both, in general, deformable and not planar. The sensor 1 includes at least one sensing unit 2, each of which responds to the local compression by increasing its capacitance. The sensing units 2 are connected to a suitable transducer 3 that converts a change in capacitance to a corresponding signal. The signal is typically a variable frequency signal whose frequency is a function of capacitance and is processed by a data processing circuit 4 to provide a measure of capacitance or a function thereof. Typically, the data processing circuit 4 samples and averages the signals and provides desired variables relating to the time variation of the local pressure applied to the sensing units 2, e.g. respiration, heart beats and variables derived from the pressure distribution as body movements.

Figure 2:
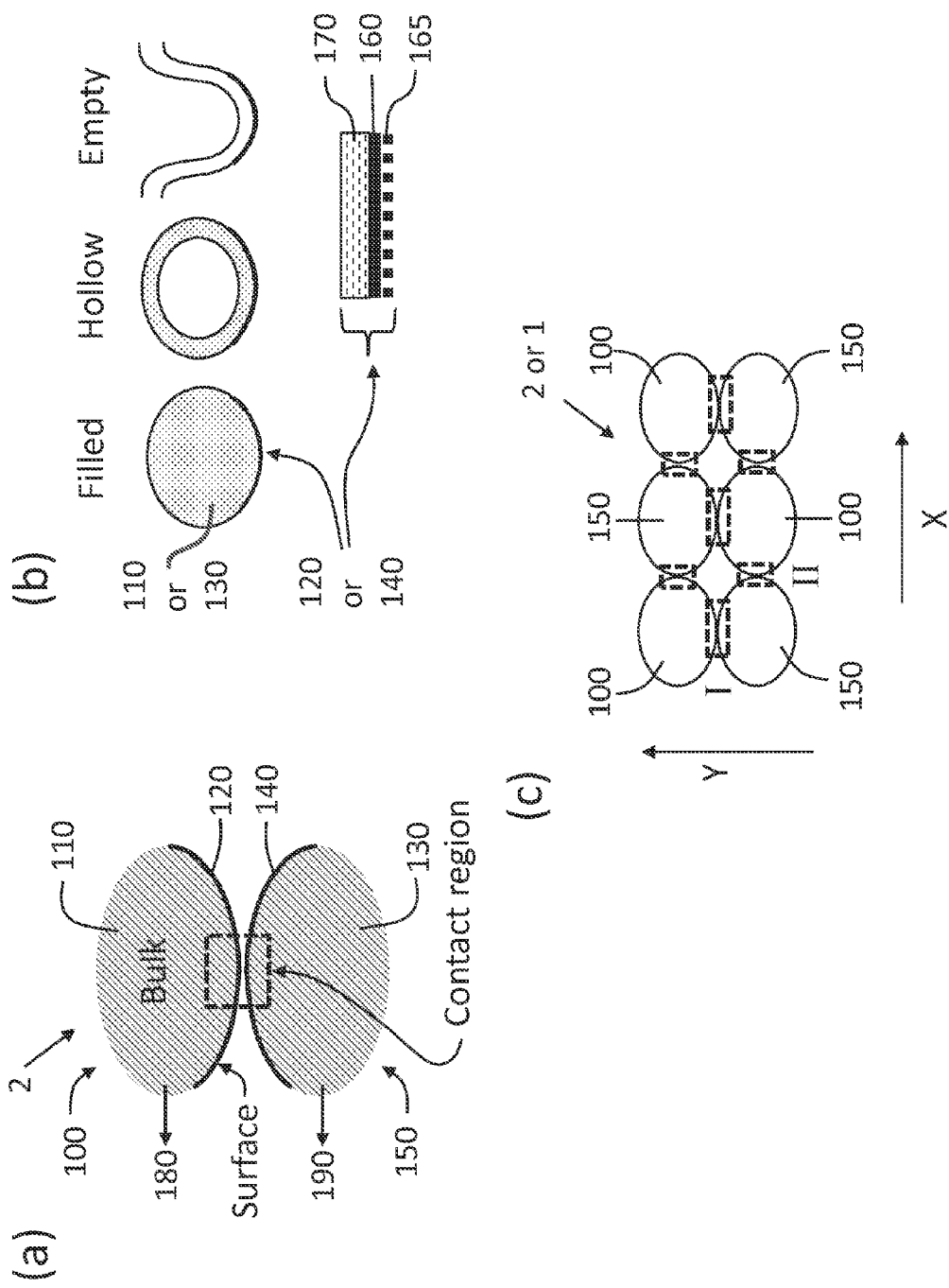
FIG. 2 is a cross-sectional view and graphical nomenclature for the structural elements of a sensing unit employed in the system of FIG. 1.

Reference is now made FIG. 2 that provides graphical nomenclature for the structural elements of the sensing unit 2 employed in the system of FIG. 1 in order to simplify the description of the various embodiments. FIG. 2a illustrates schematically the structure of the sensing unit 2 that comprises two elastic members 100 and 150, each having a deformable and elastic bulk 110 and 130, and surfaces 120 and 140, respectively. The surfaces 120 and 140 are electrically conductive, but isolated from each other by a thin elastic dielectric layer 170. The dielectric layer may be laminated on at least one of these surfaces to form an integral part of the surface, or it may be a physical barrier that separates between the two layers without reducing their elasticity. The surfaces 120 and 140 are found in contact with one another at one or more contact regions, where the total area of the contact regions increases for greater compression of the sensing unit 2. It is to be noted that surfaces 120 and 140 are conductive at least at the maximum contact region generated in the desired pressure range (marked by a thick line) and that all conductive regions in each surface are interconnected. The surfaces 120 and 140 or the bulks 110 and 130, if conductive, are connected electrically via conductors 180 and 190, respectively, to the transducer 3 that converts capacitance into data. It is worthwhile to note that at a given pressure the sensor sensitivity in detecting pressure changes is determined by the relative rate of change of the capacitance C of the sensing unit 2 with the change in pressure $\Delta P$, i.e. $(\Delta C/C(P))/\Delta P$. Since most of the capacitance of sensing unit 2 is generated at the contact regions, this sensitivity expresses the relative rate of change of the total contact area with compression.

FIG. 2b illustrates a number of optional structures that may be appropriate for the bulk and the surface of the sensing unit 2, depending on its preferred geometry and manufacturability. This may include for the bulk 110 or 130 filled or hollow structures made, for example, of injected or extruded thermoplastic elastomers foam, and open structures made, for example, from 10 malleable material, which is embossed into elastic dome-like protrusions. In case the bulk is made of electrically conductive material, e.g. conductive polyurethane foam, its surface directed towards the other bulk may be coated by a thin elastic dielectric film 160, e.g. a thermally laminated 5-30 microns elastomer film. In case the bulk is an insulator, it must be coated with an elastic and electrically-conductive layer 170, e.g. elastic and conductive fabric. It will be appreciated that only one elastic member has to include the dielectric layer 160. It is worthwhile to note that for the purpose of the present invention good electrical conductivity of the elastic members is not required, which may reduce considerably the cost of the sensor materials. Since according to the present invention the surfaces of the elastic members 110 and 130 rub against one another, there may be an advantage of adding a thin external layer 165 for reducing friction in at least the regions of potential contact between the elastic members, e.g. by adding a sprayed layer or film of Teflon.

FIG. 2c illustrates an example of a two-dimensional array of elastic members 100 and 150, wherein any neighboring pairs of elastic members 100 and 150 operates as described above with reference to FIG. 2a with different contact areas I and II along the Y and X directions, respectively, where contact I is the first to be established. Such an array may generate the flexible sensor 1 or the sensor unit 2, as shown in FIG. 1. It is self-evident that the structural concept depicted in FIG. 2c can be extended to three-dimensional arrays.

With this understanding, the embodiments disclosed hereafter can be simplified, if desired, by illustrating only surface lines; marking contact regions and omitting the electrical conductors 180 and 190. It should be noted that although FIGS. 1 and 2 show features that are known per se, to the extent that similar features are also used in different embodiments of the present invention, the same properties or alternatives are applicable also to the invention. For example, the dielectric may be deposited on one of the elastic members or it may be realized by an ultra-thin elastic barrier that separates the plates but does not reduce their ability to engage and for their respective projections to interlock.

It will also be understood that the following principles are demonstrated in a number of embodiments, which serve only for clarifying these principles, but can be implemented in other different embodiments including also combinations of embodiments.

Reference is now made to FIG. 3a that illustrates schematically the principle of operation of a known capacitive sensor 2 as shown in U.S. Pat. No. 4,986,136. The sensor comprises an electrically conductive first elastic member 100, includes a series of rounded or tapered projections 200 that may represent the cross-section of parallel structures. The projections 200 make pressure contact with a second electrically conductive flexible elastic member 150 via a dielectric layer. Under minimal pressure (denoted by an arrow), a contact region I (marked by a dotted rectangle) is established between projections 200 and the elastic member 150. FIG. 3b illustrates the deformation of the projections 200 under greater pressure. The resulting compression increases the area of the contact region I. FIG. 3c shows the variation of the capacitance C in picofarads per unit of area and the sensitivity $(\Delta C/C(P))/\Delta P$ in percent per unit of area generated by testing such a sensor 2 at the pressure range characterizing a human body on a mattress. These curves will subsequently be referred to as 'performance curves'.

FIG. 4a illustrates schematically the structure of the sensor 2 constructed and operating in accordance with an embodiment of the invention. Both elastic members 100 and 150 include respective rounded interlocking projections 200 and 250 that may, or may not have the same size and form, but are presented here as identical for the sake of simplicity. Under minimal pressure, the contact regions I are diagonal on both sides of the projections 200 and 250. FIG. 4b and FIG. 4c show that upon increasing compression, regions I increase while at some point an additional contact region II is generated. The resulting performance curves are shown in FIG. 4d. The sensitivity of this embodiment is considerably greater than that of the prior-art sensor taken from FIG. 3c and shown by dotted curve especially at low pressures, which are preferable for detecting respiration in a human lying on a mattress. It is noteworthy that the sensitivity curve can be modified by changing the gap between the projections 200 and 250, as a larger gap makes the contact region II appear earlier and vice versa.

Reference is now made to FIG. 5a that illustrates schematically the structure of the sensing unit 2 constructed and operating in accordance with another embodiment. Both elastic members 100 and 150 include rounded interlocking projections 200 and 250, respectively that have substantially the same height and nearly parallel sides. Under minimal pressure, the projections 200 and 250 touch the opposite members 150 and 100, respectively, generating the contact regions I but they do not touch each other, as shown. FIG. 5b and FIG. 5c illustrate the progressive increase in size of the contact regions I in response to increased pressure showing that at sufficiently high compression new contact regions II are formed in the vertical direction, when the projections 200 and 250 touch each other. This increases the sensitivity of the sensor unit 2 over hitherto-proposed sensors similarly to that shown in FIG. 4. It is worthy of note that for deformations of the form shown here hollow projections 200 and 250 have been found to be particularly effective.

Reference is now made to FIG. 6a that illustrates schematically the structure of the sensing unit 2 constructed and operating in accordance with another embodiment, which is different from that illustrated in FIG. 5a in one aspect: The height of the projections 200 is smaller than that of the projections 250. As a result, under minimal pressure, contact region I is generated on the elastic member 100 only. FIG. 6b shows that at elevated pressure, contact region II is generated on the elastic member 150. FIG. 6c shows that under further compression additional contact regions III are generated, of the type illustrated in FIG. 5c. FIG. 6d shows the pressure dependency of the capacitance per cm$^2$ and the sensitivity of the sensor unit 2, which is far greater that prior art sensors (dotted line) and of the embodiment shown in FIG. 4d.

Reference is now made to FIG. 7a that illustrates schematically the structure of the sensing unit 2 constructed and operating in accordance with another embodiment. Here also, there are provided a pair of mutually interlocking elements but they differ from those illustrated in FIG. 3a (prior art) in the following respects: The elastic body 100 is not flat but includes concave structures 200 that enclose complementary convex structures 250 provided in the elastic member 150. As explained previously, both the concave and the convex structures 200, 250 may be regarded as projections. The contact region I is generated under minimal pressure. FIG. 7b illustrates the mutual deformation of elements 200 and 250 under greater pressure that increases the contact region I. FIG. 7c illustrates a unique property of this embodiment—detecting forces applied at different angles, a case relevant to pressures exerted by the edge of the human body on a deformable support, such as a mattress. Such sensor location appears to be most sensitive for detecting respiration. FIG. 6d shows the performance curves of this embodiment. The sensitivity is greater than prior art sensors at low pressures, but similar and even lower at higher pressures. It is noteworthy that the sensitivity of this sensing unit at low pressures is controlled by the difference between the curvatures and elasticity of elements 200 and 250 at region I. By making the curvatures of units 200 and 250 close, even a small pressure will increase considerably the area of the contact region I, which means large low-pressure sensitivity.

Figure 8:
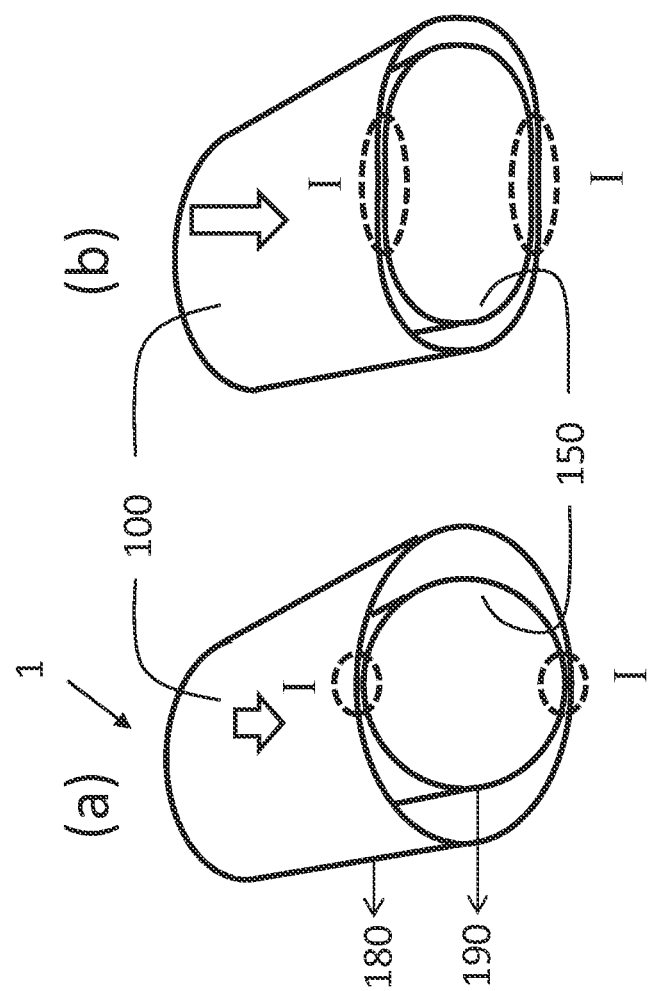
FIG. 8 is a perspective view of the sensing unit employed in the system of FIG. 1, in accordance with another embodiment of the present invention.

Reference is now made to FIG. 8a that illustrates schematically the structure of the sensor 1 constructed and operating in accordance with another embodiment, which shares some similarity with the embodiment illustrated in FIG. 7. It comprises a cylindrical elastic member 150 with a circular cross-section enclosed by an elastic member 200 in the form of a hollow cylinder with a circular or elliptic-like cross-section of larger dimensions than those of the member 150, such that under minimal pressure elastic members 100 and 150 form contact regions I. The electrical conductors 180 and 190 are marked schematically. The increase of the contact regions I at greater pressures and the rationale for enhanced low-pressure sensitivity, are the same as disclosed in the previous embodiment shown in FIG. 7. This sensor unit is self-contained and can be used in applications that favor pressure detection over a relatively large distance along a line. Both members 100 and 150 can be preferably manufactured in the form of cylinders by extrusion. While member 150 has to be hollow, member 100 may be filled to assure mechanical stability of the sensor under bending. The unloaded sensor 1 has minimal capacitance generated by the random contacts between the members 100 and 150. This is an important issue when the pressure is applied only in part of the sensor 1. This embodiment responds to forces applied in all directions that are not parallel to its axis.

Figure 9:
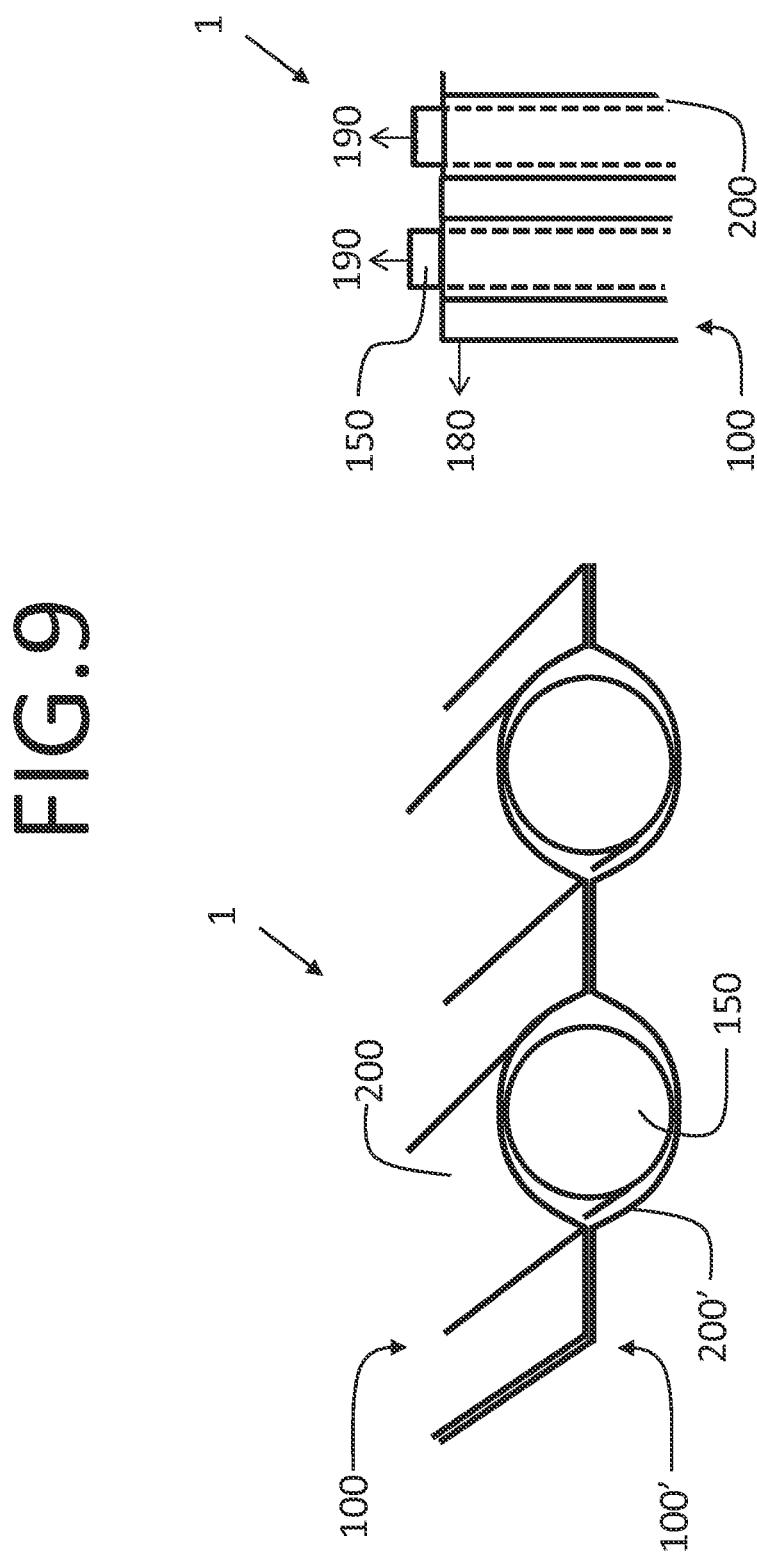
FIG. 9 includes a perspective- and top view of the sensing unit employed in the system of FIG. 1, in accordance with another embodiment of the present invention.

Reference is now made to FIG. 9 that illustrates schematically perspective and top views of the sensing unit 2 structure constructed and operating in accordance with another embodiment. This embodiment shares some similarity with the embodiments shown in FIG. 7 and FIG. 8, but differs by the following feature: Two elastic members 100 and 100' each having mutually aligned outwardly-directed projections 200 and 200' are juxtaposed back to back so that the respective projections of the two members form 'tunnels' that enclose tubular elastic members 150. The elastic members 100 and 100' can be manufactured according to the options detailed in FIG. 2b. This embodiment may be appropriate for a relatively large sized sensing unit 2. The figure also illustrates schematically the location of the electrical conductors 180 and 190, where the conductor 180 is common to both elastic members 100 and 100', while each of the elastic members 150 has its own conductors 190. In this way, a weighted average of pressure applied along a line can be detected.

Figure 10:
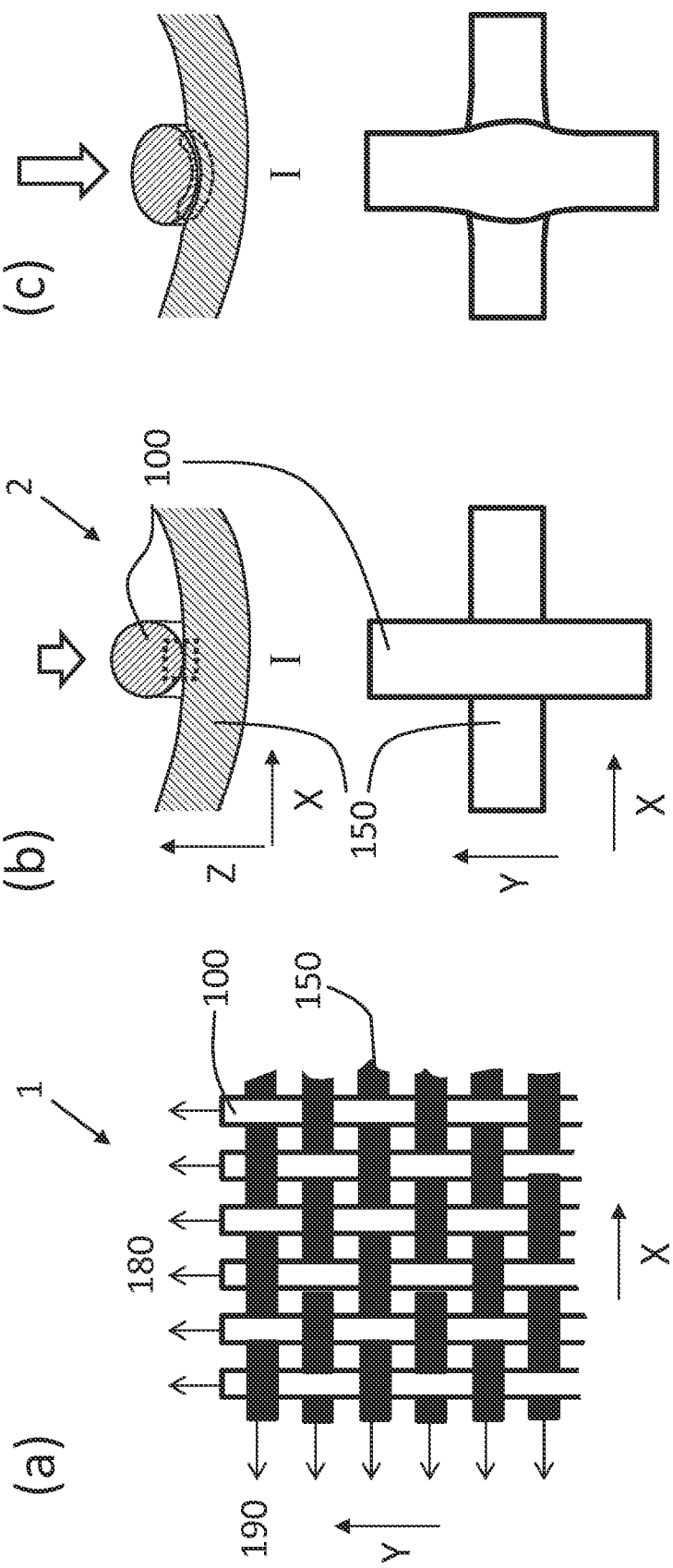
FIG. 10 includes a cross-sectional- and top view of the sensing unit employed in the system of FIG. 1, in accordance with another embodiment of the present invention.

Reference is now made to FIG. 10a that illustrates schematically a top view of a flexible sensor 1 (or sensing unit 2) with a plain weave structure constructed and operating in accordance with another embodiment. All the elastic members 150 are illustrated as black stripes in the X direction, while the elastic members 100 are in the Y direction. FIG. 10b illustrates the crossing point of the elastic members 100 and 150 in cross-sectional view (top) and top view (bottom). This crossing point is the basic sensing element of the sensor, under zero or minimal pressure, where the curvatures of the members 100 and 150 in the X-Z or Y-Z planes are conceptually similar to the ones illustrated in FIG. 7. FIG. 10c shows the same structure under elevated pressure that increases the area of the contact region I. The contact region has a three-dimensional form of a saddle. In this embodiment, the sensor is preferably made of flexible fibers having a circular cross-section to assure mechanical stability and can be manufactured by extrusion following the options presented in FIG. 2b. A textile-like sensor of this kind is extremely flexible and responds to both compression applied at some angle around the Z direction and to tension applied along the X or Y axes. It is noteworthy that the sensor sensitivity at low pressures increases with increasing density of weave structure, as member 150 becomes more wrapped around member 100 and vice versa (FIG. 10b top).

It will be appreciated that other types of weave structures can be constructed along the principles described here by those who are skilled in the art.

Figure 4:
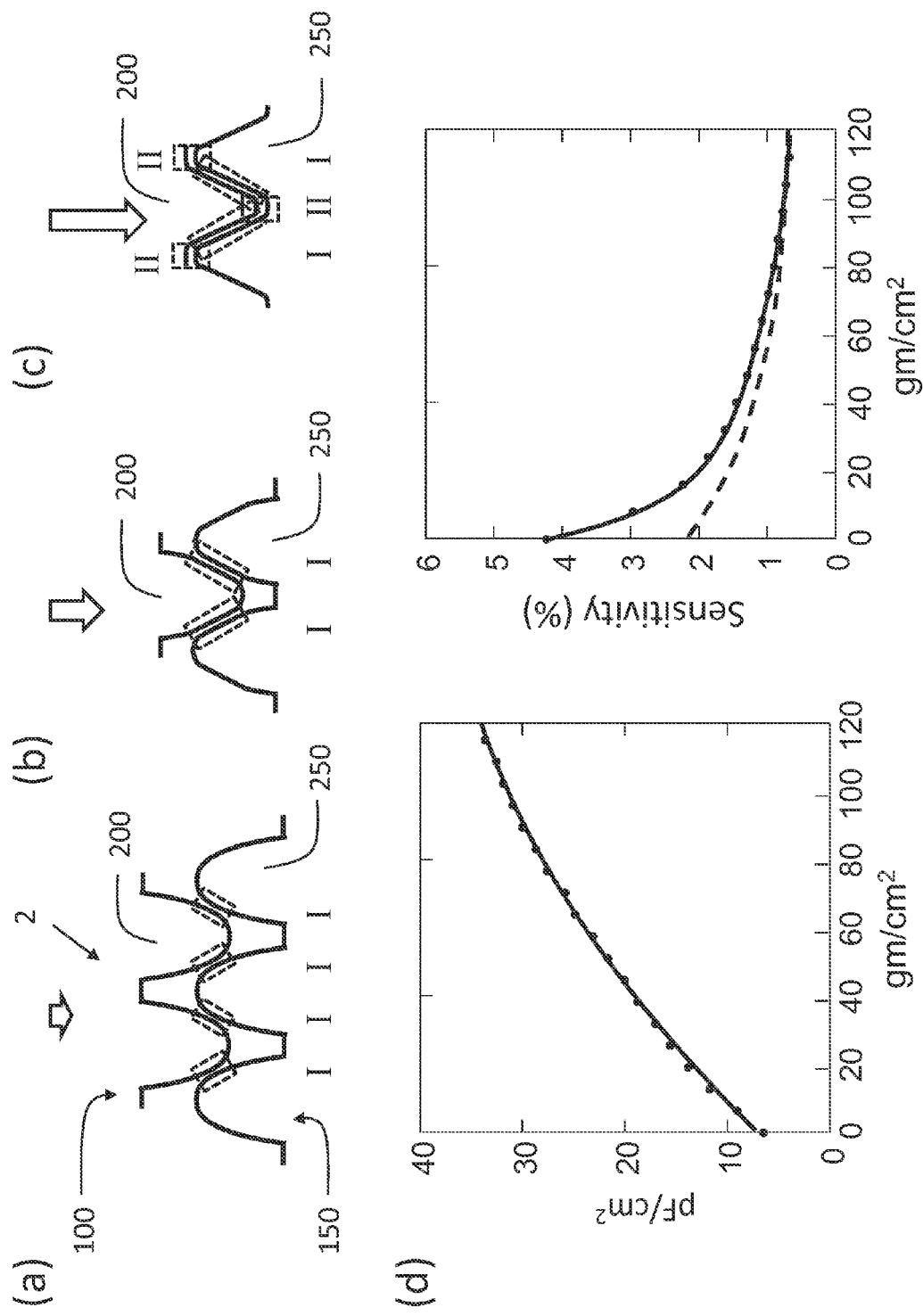
FIG. 4 includes a cross-sectional view of the sensing unit employed in the system of FIG. 1 and graphs that depict its performance under variable pressure, in accordance with one embodiment of the present invention.
Figure 11:
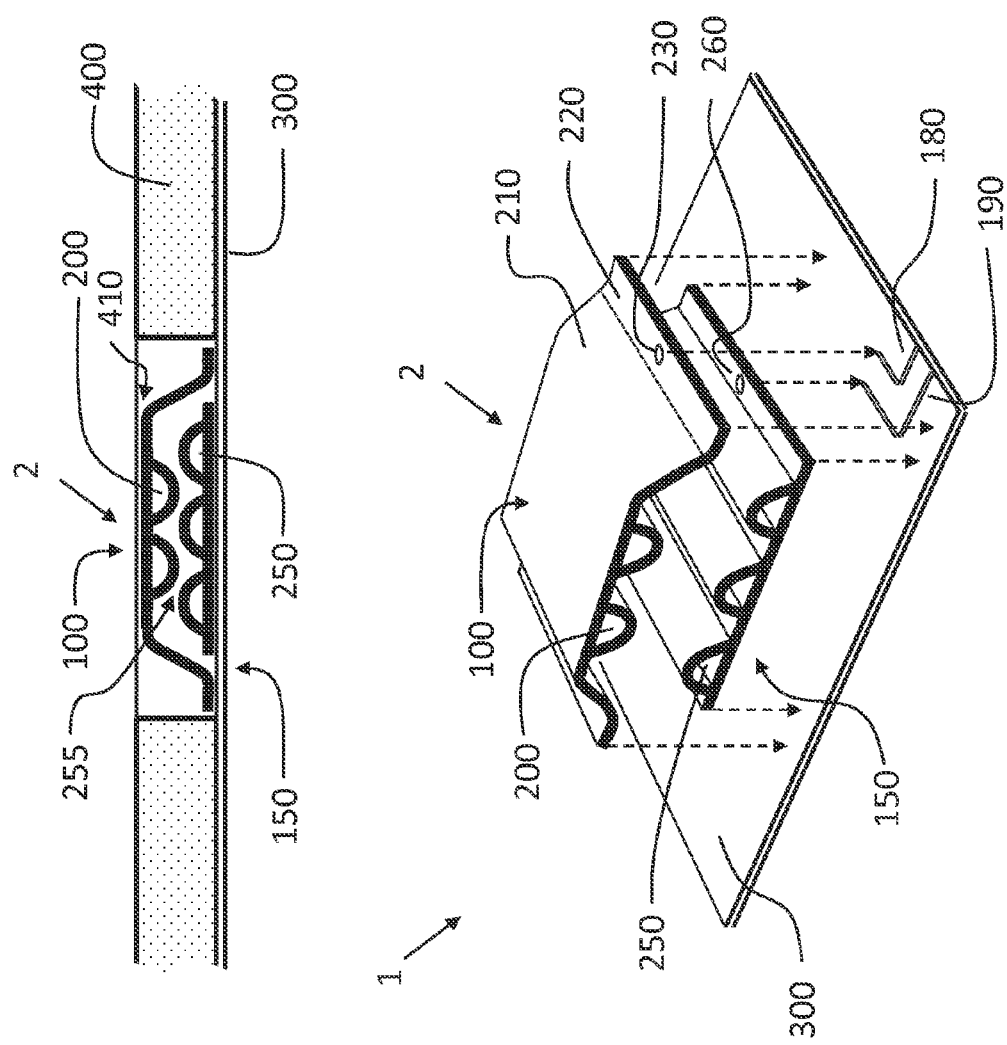
FIG. 11 includes a sectional- and exploded perspective view of the sensing unit employed in the system of FIG. 1, as described in FIG. 4, in accordance with another embodiment of the present invention.

Reference is now made to FIG. 11 that illustrates an exploded- and a cross-sectional view of one example of the sensing unit 2 as described in FIG. 4, embedded in the flexible sensor 1, constructed and operating in accordance with an embodiment of the invention. The flexible sensor 1 includes a nonconductive elastic sheet 300, to which the sensing unit 2 is attached in a mechanically stable way, and which contains the electrical conductors 180 and 190. The elastic member 150 includes a flat base attached to the elastic sheet 300 and hollow projections 250. The elastic member 100 has a flat top and the hollow projections 200, diagonal sides 210 and a base 220 attached to the elastic sheet 300. Elastic members 100 and 150 are electrically connected to the conductors 180 and 190, respectively, e.g. via rivets at points 230 and 260, without forming an electrical contact with each other. The appropriate options for the surface structure of the elastic members are as described above with reference to FIG. 2b. The structure of the elastic member 100, as shown, enables the capacitance of an unloaded sensing unit 2 to be minimized by keeping an initial gap 255 between projections 200 and 250 as shown. In order to distribute the applied pressure homogeneously over the flexible sensor 1, the elastic sheet 300 is covered with a sensor cushion 400, which may be foam or any elastic structure, preferably having thickness versus pressure dependency similar to that of the sensing unit 2 and being embedded in appropriately sized bores in the sensor cushion 400. Preferably, the unloaded thickness of the cushion 400 is somewhat larger than that of sensing unit 2, which leaves a gap 410 that determines together with gap 255 the minimal pressure required for generating the contact region.

Figure 5:
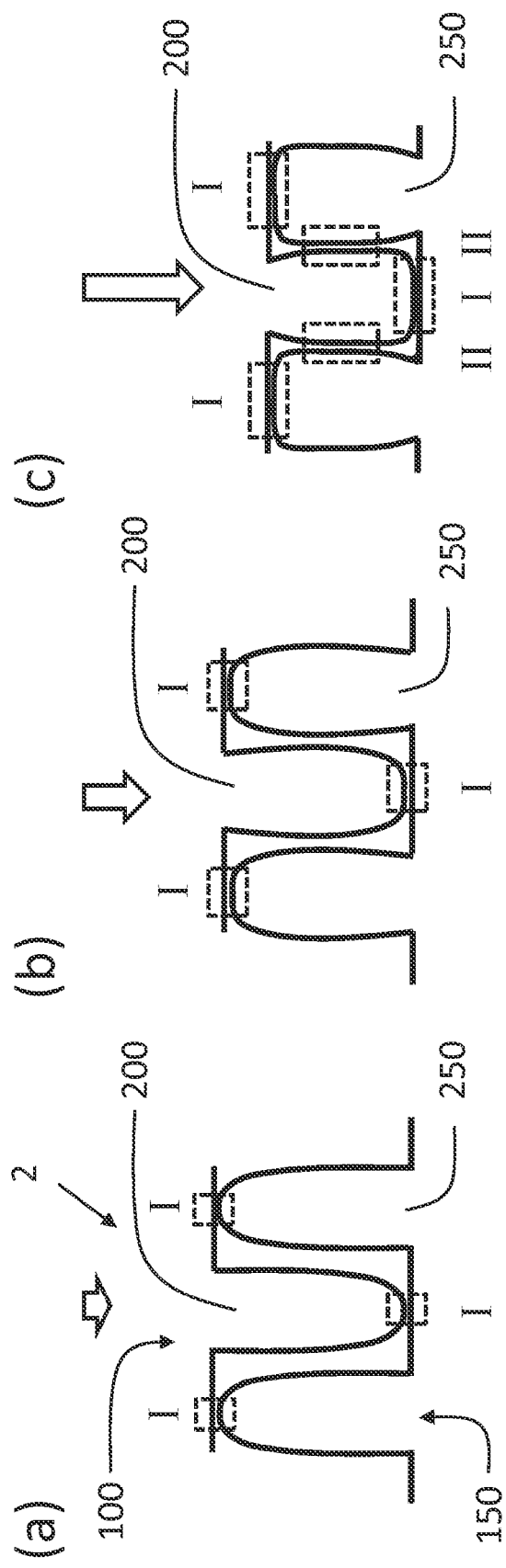
FIG. 5 is a cross-sectional view of the sensing unit employed in the system of FIG. 1, in accordance with another embodiment of the present invention.
Figure 6:
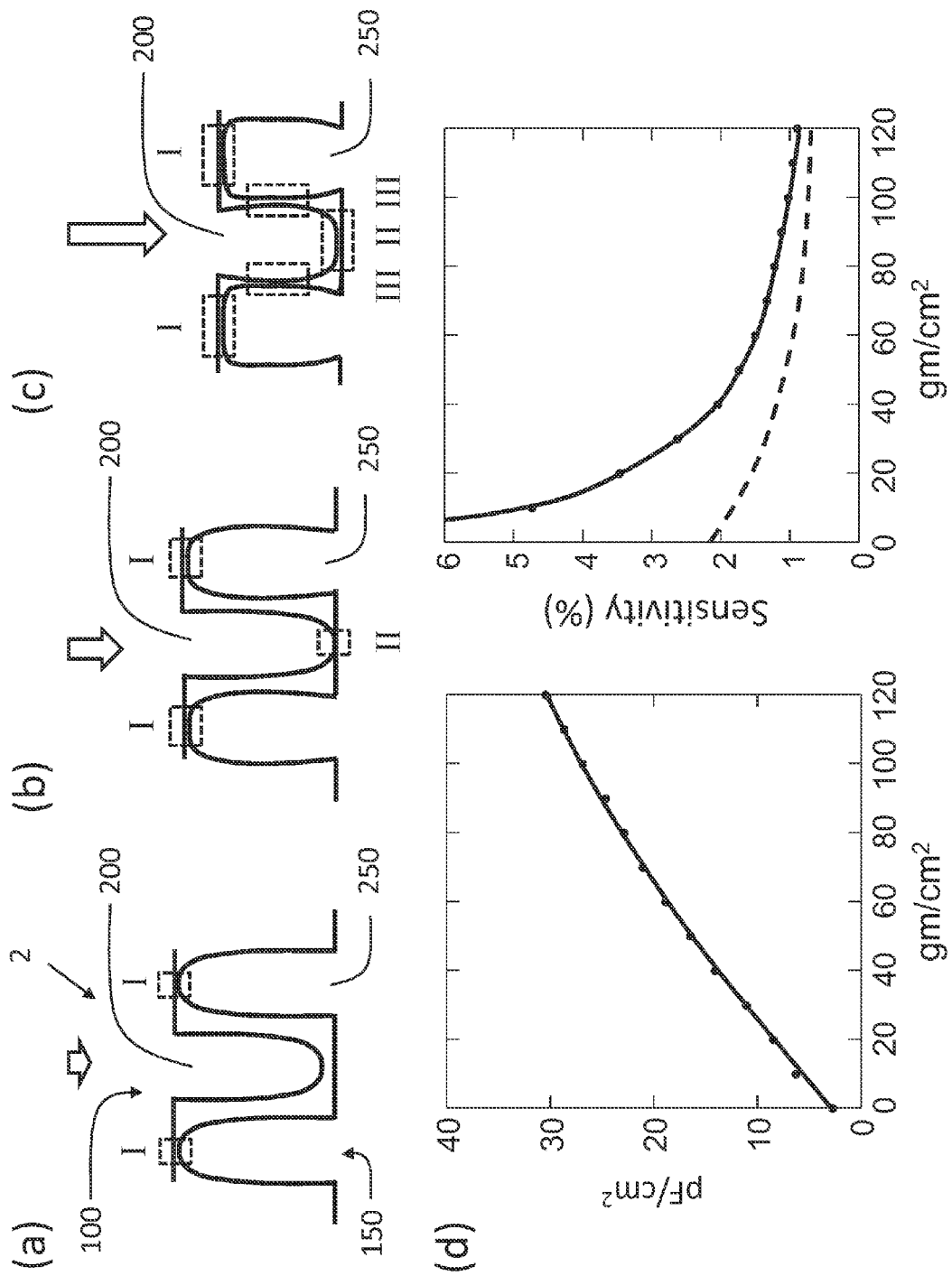
FIG. 6 includes a cross-sectional view of the sensing unit employed in the system of FIG. 1 and graphs that depict its performance under variable pressure, in accordance with another embodiment of the present invention.

It will be appreciated that the embodiment illustrated by FIG. 11 can be used also with the structure of the sensor unit illustrated in FIG. 5 and FIG. 6. In another implementation similar to the one described in FIG. 11the projections 250 can have the form of half ellipsoids that can be embossed in an elastic sheet 300 made of thermoplastic elastomer previously covered by elastic and conductive fabric and a dielectric layer at selected functional domains according to the principles described in FIG. 2.

Figure 12:
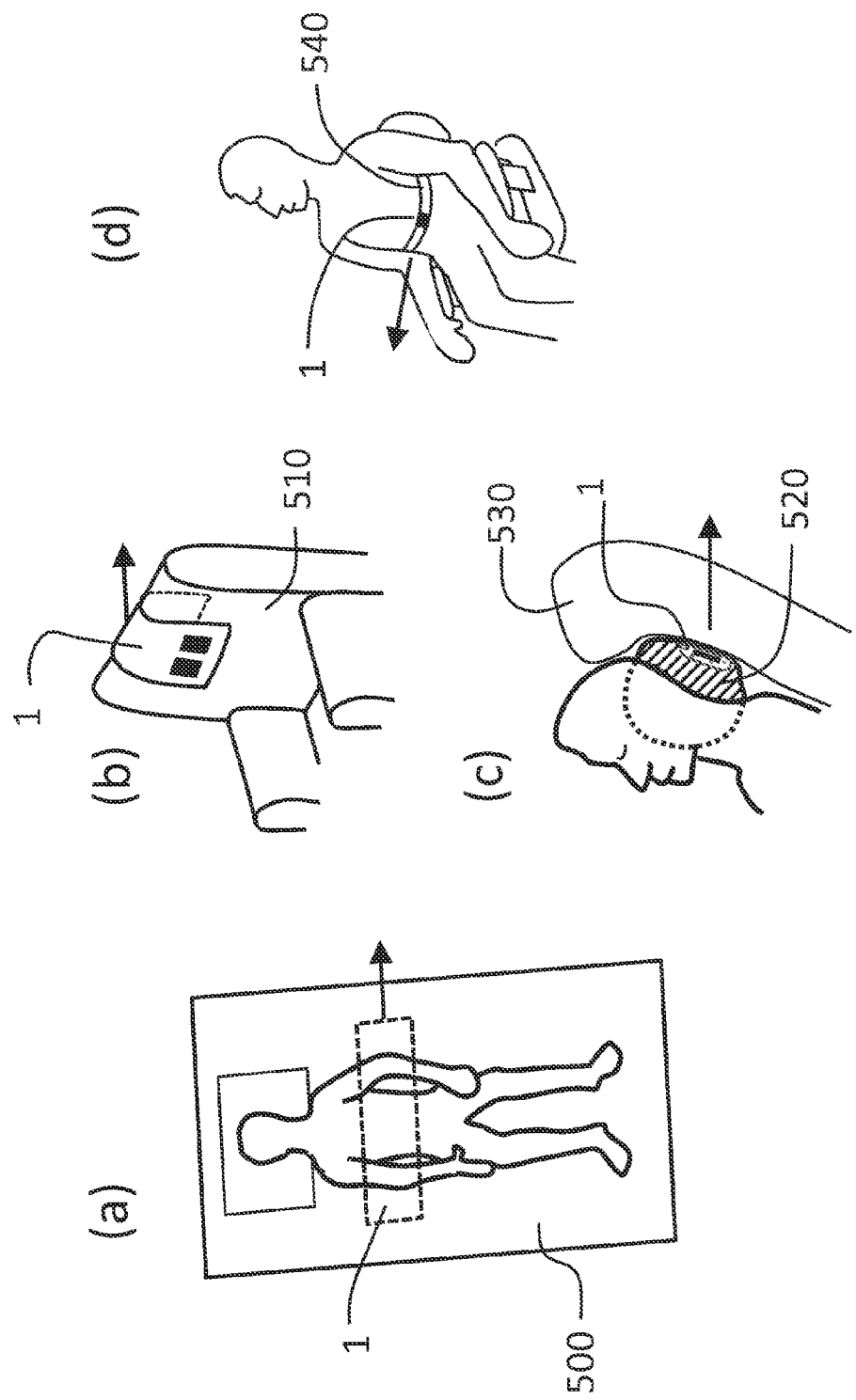
FIG. 12 includes perspective view of the sensing unit employed in the system of FIG. 1 attached to a user or appliance in a number of embodiments of practical interest, in accordance with embodiments of the present invention.

Reference is now made to FIG. 12 that illustrates four embodiments, in which the user's body subjects the flexible sensor 1 to pressure, a small part of which is caused by pressure variations generated by respiratory movements. The sensor output (marked by an arrow) may serve as an input to products that require high-quality monitoring of the respiration pattern.

FIG. 12a illustrates the flexible sensor 1 in the form of a pad placed on mattress 500 over or under the sheet and under the user's torso when lying in a dorsal position, prone position or lateral position,. The sensor may include single or multiple sensing units 2 (not shown). It will be appreciated that such a pad sensor can have the form of a sheet that covers the whole mattress. Furthermore, the sensor pad can be placed below or under pillows having a structure that causes respiratory-related head movements.

FIG. 12b illustrates a similar sensor pad placed freely on the back of a sofa 510, in a way that the sensing units are located against the back of the user. FIG. 12c illustrates a neck support pillow for travel 520 that is compressed by the user's neck against the back of a head/back support chair 530. The sensing unit 2 is attached to or integrated into the neck support pillow 520. FIG. 12d illustrates an elastic belt sensor 540 worn typically around the torso that converts the torso circumferential changes induced by the breathing movements into stretch variations in the belt. A sensing unit 2 integrated into the belt is stretched and compressed simultaneously. It is appreciated that the selection of the specific sensor unit 2 for a specific application depends on the type, magnitude, directionality and spatial spread of forces involved and the desired variables.

Figure 13:
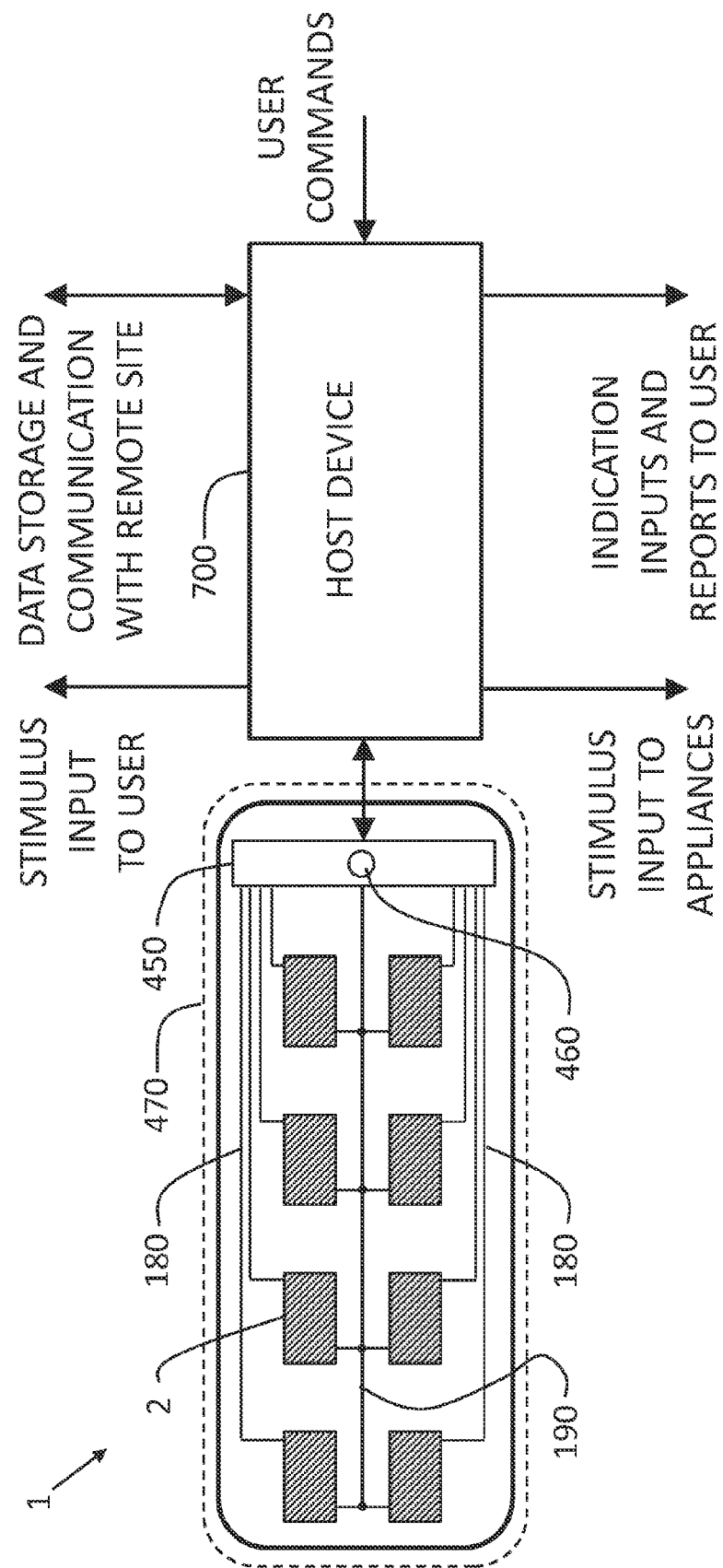
FIG. 13 includes schematic top view and block diagram of the flexible sensor employed in the system of FIG. 1 and its outcomes emerging via a host device, in accordance with embodiments of the present invention.

Reference is now made to FIG. 13 that illustrates schematically the general structure of a flexible sensor 1 containing at least one sensing unit 2 constructed and operative in accordance with an embodiment of the invention. The sensing unit 2 includes a sensor that communicates bi-directionally and preferably wirelessly with a host device 700, preferably a mobile phone, via a specialized Application ('App') or with any other device having similar functionality, e.g. iPad, iPod, laptop etc. It is appreciated that wired communication via a cable is also possible.

Each of the sensing units 2 serves as an input to the sensor circuit 450. In practice, one of the electrical conductors 180 or 190 may be common to all sensing units 2, as shown. The electronic circuit 450 performs at least the function of capacitance conversion into data for selected sensing units 2 and may also handle some of the data processing and bi-directional communication with the mobile phone 700.

The electronic circuit 450 is energized preferably by disposable or rechargeable batteries. A button 460 may be provided for manual activation or deactivation of the system, whose state can be indicated to the user by an arrangement of dynamic LEDs, if desired. The flexible sensor 1 and the electronic circuit 450 are preferably enclosed by a cover 470 that protects the various sensor parts and makes the sensor comfortable and aesthetic according to the application, e.g. it is preferably machine washable for the application shown in FIGS. 12a and 12b.

The host device 700, preferably a mobile phone, may further process the sensor data for the following purposes: i) calculating desired variables including, for example, single- and multiple respiration pattern characteristics and body movements that may be useful, for example, in determining the sleep structure and quality and markers for abnormal breathing; ii) controlling the operation of the electronic circuit 450 in response to the analyzed data and user commands, and providing indication inputs and feedback to the user, e.g. the status of sensor connectivity with the App, status of the battery charge and status of respiration detection and the level of variation of respiration characteristics over time; iii) generating from the processed data stimuli inputs to the user in order to modify respiration pattern by generating guiding to breathing movements via tones or other stimulations, as disclosed by the present inventor in U.S. Pat. Nos. 5,076,281 and 5,800,337 to induce, for example, relaxation, or stimulations intending to elicit alertness, e.g. waking up a user upon detecting a prolonged apnea; iv) storing data and communicating with remote site including, for example, uploading to the iCloud both raw and analyzed data, sharing data with other users and communicating with technical support over the internet, etc.; and v) providing stimuli to appliances in response to measures generated by the data analysis, which is possible in the so-called 'smart home'. For example, the App may turn on/off lights and radio accordance to the detected sleep phase, or turn on minimal light when a user leaves bed at night and thus unloads the sensor.

Figure 14:
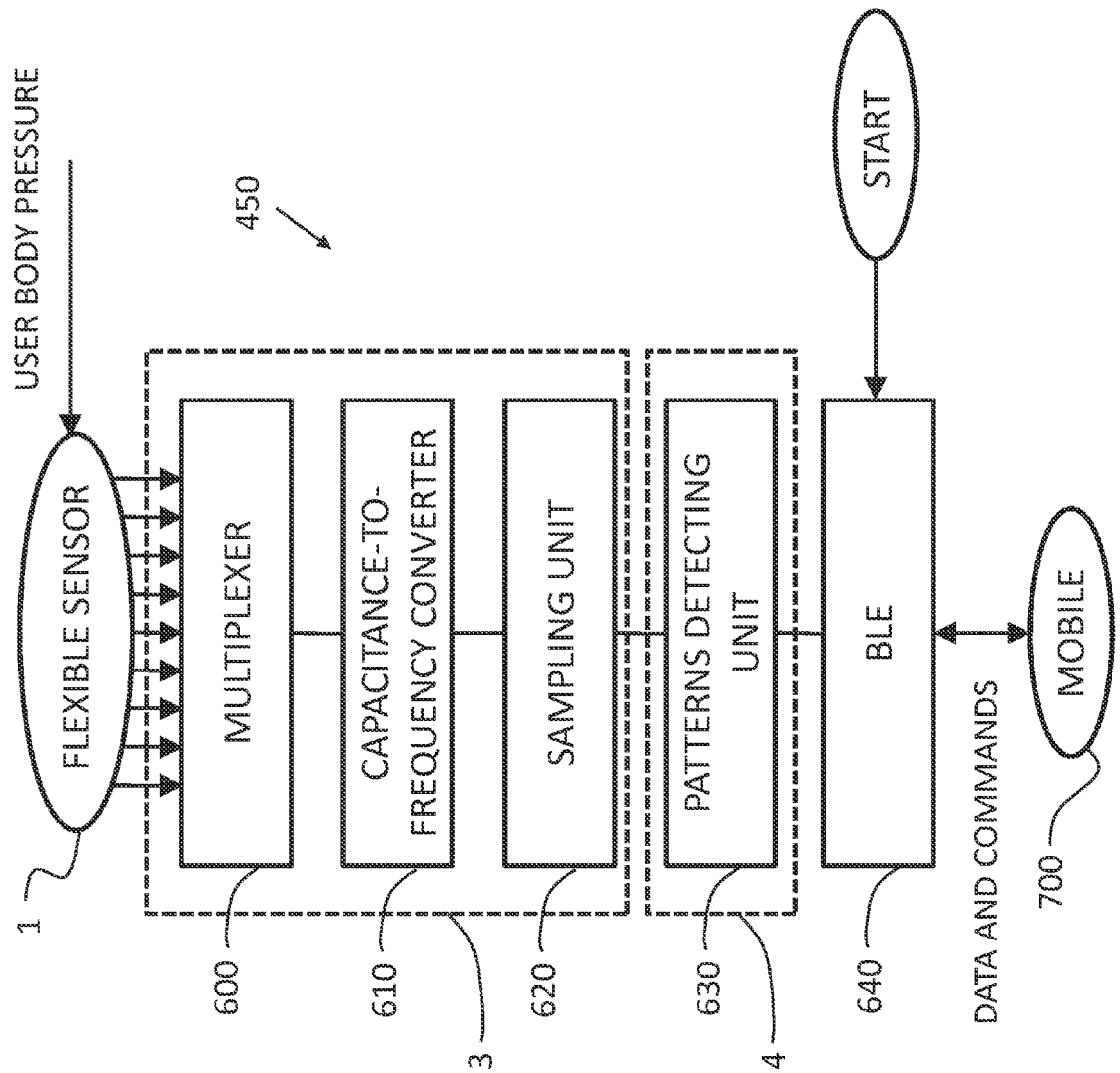
FIG. 14 is a block diagram showing the functional units employed in the system of FIG. 1, in accordance with one preferred embodiment of the present invention.

Reference is now made to FIG. 14, which is a block diagram showing the functional units of the electronic circuit of an embodiment illustrating the operation of a monitor employed in the system of FIG. 13 in case of wireless communication with a mobile phone 700. A multiplexer 600 connects the different sensing units to the capacitance-to-frequency converter 610 following a selected order and timing. The conversion can be made by standard methods, e.g. Schmidt trigger inverter oscillator, where the output frequency is reciprocally related to the sensing unit capacitance, and thus related functionally to the pressure exerted on the sensing unit, as illustrated, for example, by FIG. 6d.

The sampling unit 620 samples this frequency in a given time window and may average several consecutive samples to obtain the average frequency per sensing unit at this time point.

Units 600, 610 and 620 establish the capacitance-conversion-into-data circuit 3 shown in FIG. 3. These data are analyzed by a pattern-detecting unit 630, which derives the desired variables. Unit 630 is equivalent to the data processing circuit 4 shown in FIG. 3. The data, including desired variables and various status indicators, are transmitted wirelessly to the mobile phone 700 preferably via a Bluetooth™ low energy chip (BLE) 640. It is appreciated that the function of the pattern-detecting unit 630, all of it or in part, may also be performed by the mobile phone 700, as described above. The BLE receives from the mobile phone 700 commands including parameters that control the operation of the other units comprising the electronic circuit 450. The START command may be provided to the BLE manually, for example, by pressing the button 460 or by loading the flexible sensor 1, provided that the electronic circuit 450 is in a 'sleep' state. It is appreciated that in case of a single sensing unit, e.g. in the case of a belt sensor illustrated in FIG. 12d, no multiplexer is needed.

Figure 15:
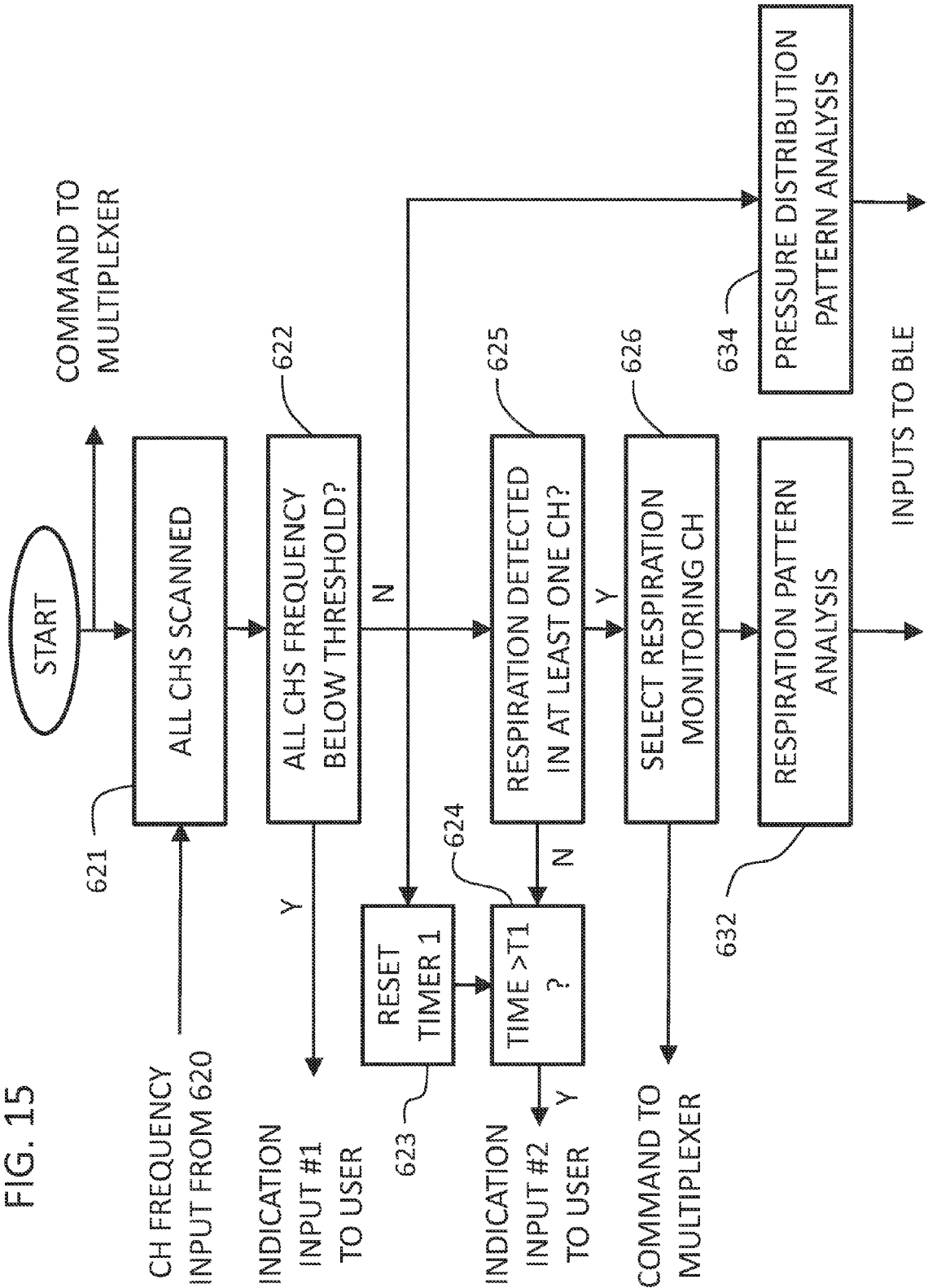
FIG. 15 is a block diagram showing an example of the processes involved in getting desired variables from the sensing unit data with reference to the functional units employed in FIG. 14, in accordance with one preferred embodiment of the present invention.

Reference is now made to FIG. 15, which is a block diagram showing an example of the processes involved in getting desired variables from the frequency signal corresponding to the capacitance measured by the sensing unit 2, as generated by sampling unit 620 and will be called hereafter 'channel' (CH). This diagram is constructed in accordance with the embodiments of the present invention illustrated in FIG. 15. Upon START all channels are scanned cyclically by unit 621 following a command given to the multiplexer. If the frequency of all channels is below a given threshold, it means that no load was placed on the flexible sensor 1. This may happen, for example, if the user turns on the system shown in FIG. 12a prior to entering bed, or leaves the support (FIGS. 12a and 12b) during use of the system, or when the belt shown in FIG. 12d 20 becomes loose. In any of these cases unit 622 will provide an indication input #1 to the user for clarifying the situation. In case unit 622 finds that at least one CH frequency is greater than the threshold, i.e. at least one sensing unit 2 is loaded, then three processes start simultaneously: i) Unit 625 analyses all CHs representing loaded sensing units in an attempt to detect CHs that may represent respiration activity. Such analysis is disclosed, for example, in U.S. Pat. No. 5,800,337; ii) providing a time limit to this analysis by activating a timer unit 623. In case the user places the flexible sensor 1 in a location at which respiratory movements cannot be detected, the time will exceed a predetermined threshold T1 (unit 624) and the user will be notified by indication input #2; iii) providing the value of all channels in predetermined time intervals. These values refer to time-dependent pressure distribution generated by the user body on the flexible sensor 1. The variation of the distribution over time may be used for monitoring the body movements that are known to be associated with sleep structure and quality. This task is handled by unit 634. In case unit 625 detects respiration activity in a number of channels, unit 626 selects the most appropriate CH for respiration monitoring, e.g. selecting the CH with the largest stability or signal-to-noise ratio. In case the time variation of the pressure distribution determined by unit 634 is much slower than that required from respiration, or is of no interest, the unit that selects the respiration monitoring CH may provide a command to the multiplexer to connect only the selected CH. It is to be noted that the present flowchart is applied continuously, so any loss of detected respiration restarts the relevant part of the process required for detecting respiration. The data provided by units 632 and 634 (both raw and analyzed) serve as inputs to the BLE. It is appreciated, that all or some parts of the flow chart can be handled by the host device 700, in general or mobile phone, in particular, and the BLE role is just transmitting the channel's frequency generated by unit 620. It is also appreciated that in the case where the flexible sensor 1 includes a single sensing unit 2 no multiplexer is needed and there are other obvious simplifications in the schemes presented in FIG. 14 and FIG. 15.

Figure 16:
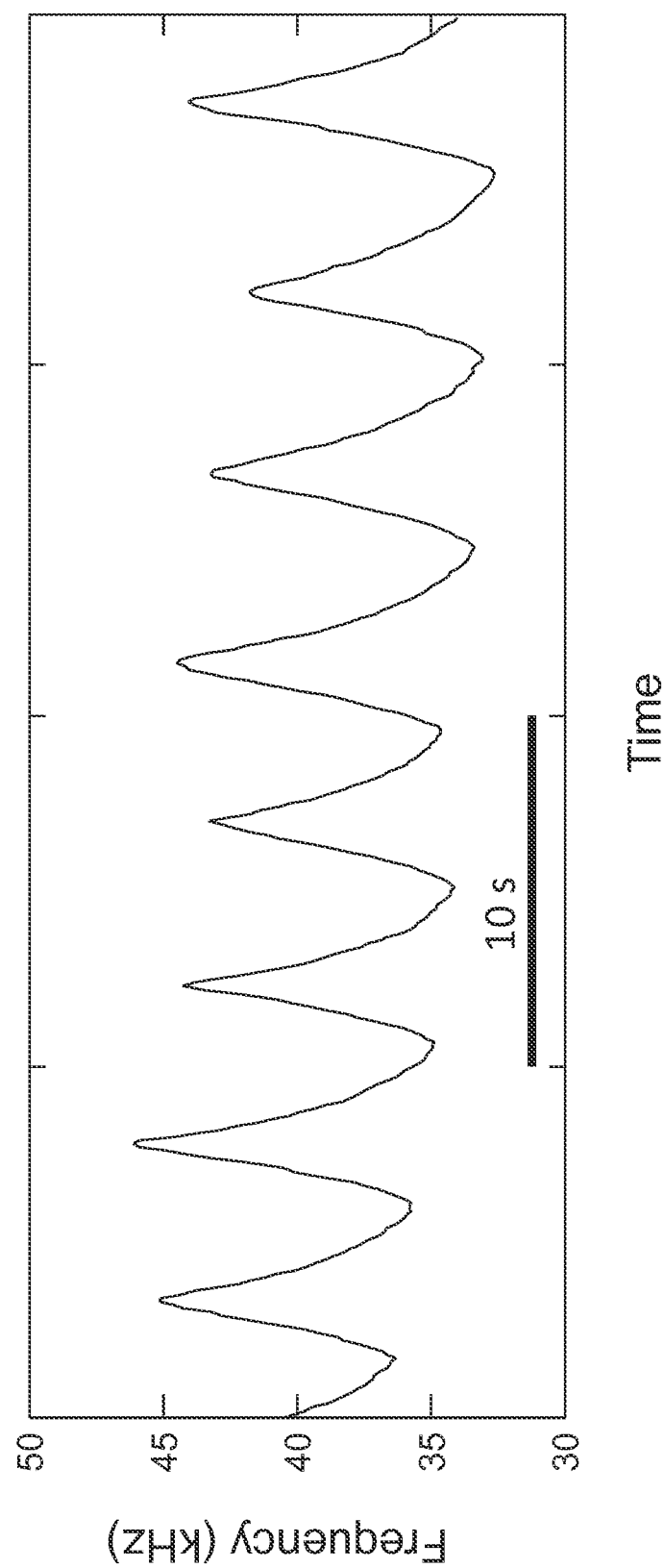
FIG. 16 is a graph showing a typical respiration signal expressed as variation over time in the frequency obtained from the capacitance of the sensing unit, in accordance with an embodiment of the invention.

Reference is now made to FIG. 16 that illustrates a typical respiration signal of a user under spontaneous breathing expressed as variation over time in the frequency obtained from the capacitance of the sensing unit 2, in accordance with an embodiment of the invention. It is noteworthy that the respiration amplitude is about 3% of the average frequency that corresponds to pressure of about 15 gm/cm$^2$ this being the low-pressure range at which the sensing units constructed according to the invention are especially sensitive. Furthermore, the respiration signal as shown represents the raw data to which no filtration or other processing has been applied.

It will be appreciated that the flexible sensor 1 may frequently detect heartbeats in a way that enables to determine heart rate. However, this may not be an optimal way of detecting heartbeats. Therefore, it will also be appreciated that additional sensors can be integrated into the flexible sensor 1. For example, piezo films that monitor effectively heart rate and body movements. Such combinations may be important for some healthcare applications.

It will be further appreciated that the flexible sensor 1, if large enough, e.g. in the form of a sheet on a large mattress, may detect desired variable in more than one user, e.g. a mother and her child. Differentiation between users monitored simultaneously can be made easily using heart rate monitors integrated into the flexible sensor 1 at different locations.

It is to be appreciated that additional desired variables generated by the analysis of the flexible sensor 1 may be temporal correlations between dynamic variations in respiration structure (single and multiple pattern) and pressure distribution pattern. For example, coughing, vomiting and suffocation in babies are likely to be manifested by such correlations, suggesting that the invention has a potential in early detection of high-risk states that may result in death, e.g. sudden infant death syndrome (SIDS).

It is also to be noted that while various distinctions of the invention over the prior art have been mentioned, these distinctions are not to be construed as the only distinctions over the prior art.

It will be appreciated by persons skilled in the art that the present invention is not limited by what has been particularly shown and described above. Rather the scope of the present invention is defined only by the following claims.

The invention claimed is:

1. A capacitive pressure sensor comprising first and second of mutually displaceable elastic members each having a respective electrically conductive surface separated by a thin elastic dielectric, wherein:
   variations in area of pressure-induced contact between the first and second members are used to vary capacitance of the sensor that allows determination of differential pressure between the two elastic members;
   both of the elastic members have respective projections configured so that as the elastic members are pressed toward each other their respective projections progressively engage and create increasing areas of contact;
   the projections have conductive surfaces at least at a maximum contact region generated in a predetermined pressure range; and
   the conductive surfaces of the projections of the first elastic member are disposed in interlocking relationship with the conductive surfaces of the projections of the second elastic member and when the respective projections of the first and second elastic members engage each other the projections cannot be completely separated by lateral displacement along two mutually orthogonal axes.

2. The sensor according to claim 1, wherein the respective projections of the first elastic member are convex and the respective projections of the second elastic member are either convex or concave.

3. The sensor according to claim 1, wherein the respective projections of the first member have radii of curvature that point in a first direction and the respective projections of the second member have radii of curvature that point in a second direction opposite to the first direction.

4. The sensor according to claim 1, wherein the respective projections of the first and second members have radii of curvature that point in an identical direction.

5. The sensor according to claim 1, wherein the areas of pressure-induced contact are non-planar.

6. The sensor according to claim 1, wherein the first and second elastic members are tubular and the second elastic member is disposed inside the first elastic member.

7. The sensor according to claim 1, including at least one pair of said first elastic members, wherein:
   each of the first elastic members has mutually aligned outwardly-directed projections that are juxtaposed back to back so that the respective projections of the two members form tunnels that accommodate a respective second elastic member; and
   each of the second elastic members is of tubular construction.

8. The sensor according to claim 1, wherein the first and second elastic members are cylindrical and are interlocked by a weave structure.

9. The sensor according to claim 1, wherein the first and second elastic members are initially displaced from each other and are configured to make initial pressure contact only in response to pressure that is greater than a first predetermined threshold.

10. The sensor according to claim 9, wherein respective areas of the first and second elastic members that are initially displaced from each other are configured to make initial pressure contact only in response to pressure that is greater than a second predetermined threshold.

11. An apparatus for monitoring respiration or body-pressure-distribution, the apparatus comprising the capacitive pressure sensor according to claim 1.

12. The apparatus according to claim 11, being at least partially implemented by a programmable hand-held device such as a computer or smartphone.

* * * * *